United States Patent [19]
Jahrmarkt et al.

[11] Patent Number: 5,139,032
[45] Date of Patent: Aug. 18, 1992

[54] FIXED BALLOON ON A GUIDEWIRE EXTENSION WIRE SYSTEM AND KIT

[75] Inventors: Scott L. Jahrmarkt, Fort Lauderdale; Fernando M. Viera, Hialeah; J. William Box, Miami, all of Fla.

[73] Assignee: Cordis Corporation, Miami Lakes, Fla.

[21] Appl. No.: 510,522

[22] Filed: Apr. 18, 1990

[51] Int. Cl.$^5$ ............................................. A61B 5/00
[52] U.S. Cl. .................................... 128/772; 128/657
[58] Field of Search .............. 128/772, 657, 658, 898; 604/96, 280

[56] References Cited

U.S. PATENT DOCUMENTS

| | | | |
|---|---|---|---|
| 4,509,944 | 4/1985 | King et al. | 604/164 X |
| 4,813,929 | 3/1989 | Semrad | 604/51 |
| 4,827,941 | 5/1989 | Taylor et al. | 128/772 X |
| 4,846,193 | 7/1989 | Tremulis et al. | 128/772 |
| 4,860,757 | 8/1989 | Lynch et al. | 128/772 X |
| 4,875,489 | 10/1989 | Messner et al. | 128/772 |
| 4,922,923 | 5/1990 | Gambale et al. | 128/772 |

*Primary Examiner*—Max Hindenburg
*Attorney, Agent, or Firm*—Thomas R. Vigil; Henry W. Collins

[57] ABSTRACT

The extension wire for a fixed balloon on a guidewire comprises a length of extension wire and a connector assembly mounted on the distal end of the length of extension wire. The connector assembly includes a tube which is received on and fixed to a distal end of the length of extension wire and which has means within the tube for grippingly engaging an outer covering sheath of a cut proximal end of the sheath and core wire of a fixed balloon on a guidewire.

The fixed balloon on a guidewire extension wire assembly kit includes the extension wire and connector assembly at the distal end of the extension wire, and an alignment tool having a body and a throughbore adapted to receive the tube of the connector assembly at the distal end of the extension wire in one end thereof and the cut proximal end of a fixed balloon on a guidewire in the other end for guiding the cut end into the tube of the connector assembly.

The method for extending an initially inserted fixed balloon on a guidewire having a strong relief sheath and a hub at the proximal end thereof comprises the steps of:

providing an extension wire with a connector assembly at a distal end thereof, the connector assembly including a tube fixed to the distal end of the extension wire, providing gripping means within the tube;

cutting the strain relief sheath and hub from the proximal end of an initially inserted fixed balloon on a guidewire; and inserting the cut proximal end of the fixed balloon on a guidewire including a core wire and a surrounding sheath into the tube of the connector assembly to cause the gripping means therein to grippingly engage the sheath at the cut proximal end of the fixed balloon on a guidewire.

14 Claims, 4 Drawing Sheets

FIG. 1
FIG. 2
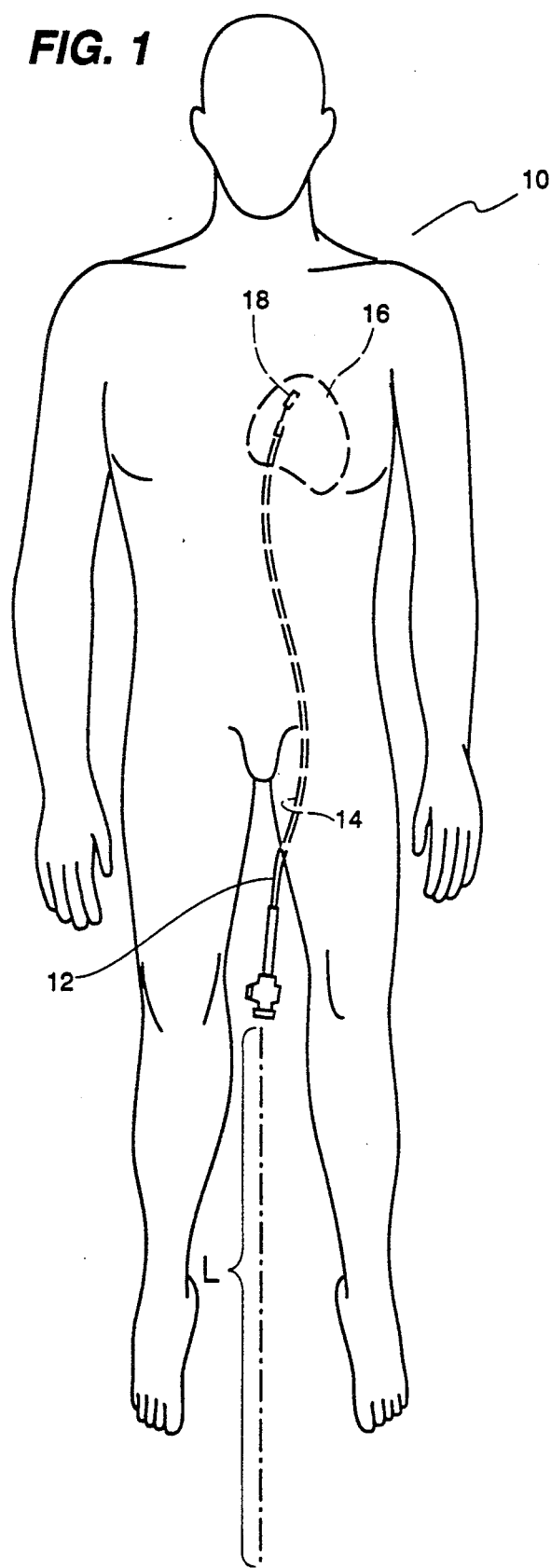
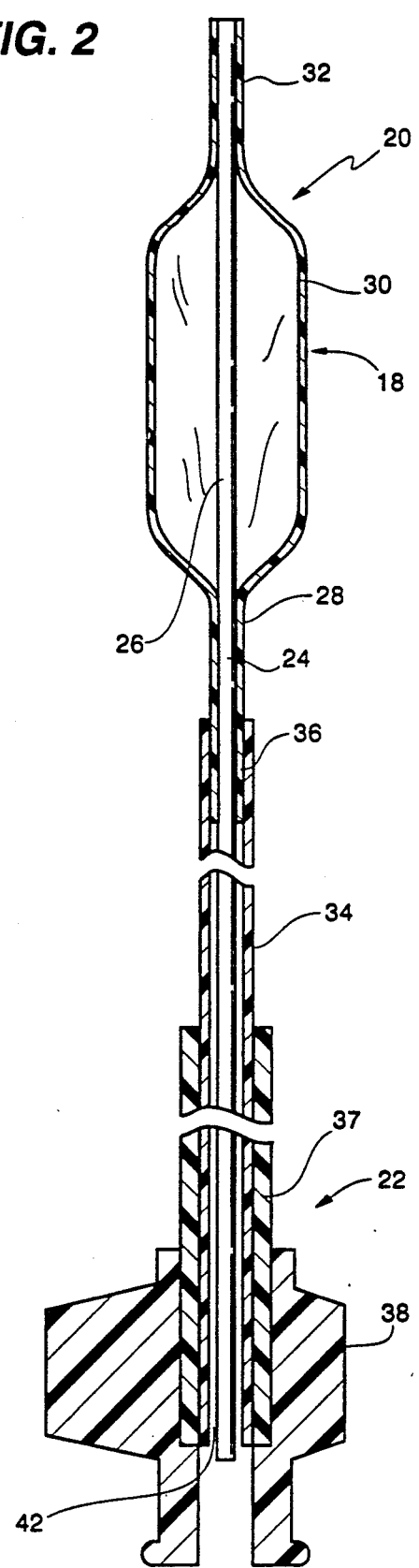

FIXED BALLOON ON A GUIDEWIRE EXTENSION WIRE SYSTEM AND KIT

BACKGROUND OF THE INVENTION

1. Field of the Invention

The present invention relates to a fixed balloon on a guidewire extension wire system and kit including an extension wire and a connector assembly for connecting the extension wire to the proximal end of a vascularly inserted fixed balloon on a guidewire whereby a guiding catheter can be inserted over the extension wire and the inserted fixed balloon on a guidewire for inserting the guiding catheter into the vascular system after which the fixed balloon on a guidewire and extension wire can be removed and another fixed balloon on a guidewire or a dilatation balloon catheter can be inserted through the guiding catheter for placing a new balloon in an area of stenosis.

2. Description of the related art including information disclosed under 37 CFR §§ 1.97-1.99

Heretofore, it has been proposed to provide an exchange guidewire which, after removal of a shorter primary guidewire, is inserted through a dilatation balloon catheter situated in a guiding catheter inserted in a femoral or carotid artery for the purpose of replacing the dilatation balloon catheter.

Since the procedure of utilizing an exchange guidewire is tedious, painstaking, time consuming and has some risk involved, it has also been proposed to utilize a guidewire extension for introducing a new dilatation catheter into a cardiovascular system.

For example, there is proposed in U.K. Patent Application No. 2 180 454 a guidewire system where the proximal end of an initial or primary guidewire is received in a sleeve which is also received over the distal end of an extension wire and the sleeve is crimped to fix the mating ends of the guidewire and extension wire together.

Also, an extendable guidewire system has been proposed in U.S. Pat. No. 4,827,941 wherein a small diameter proximal end portion of a primary guidewire is frictionally received within a tubular member fixed to a distal end of a guidewire extension section.

Further, an extendable guidewire for introducing a dilatation catheter into a cardiovascular system has been proposed in U.S. Pat. No. 4,875,489 where the proximal end of a main guidewire has a tapered end portion which is received into a tubular member having a slit or slot therein which permits it to expand, the tubular member being received within an outer sleeve and fixed to a reduced in diameter distal end of a section of an auxiliary guidewire.

However, the provision of an extension wire for a fixed balloon on a guidewire has not heretofore been proposed, particularly since the fixed balloon on a guidewire has a hub and strain relief sleeve on the proximal end thereof.

As will be described in greater detail hereinafter, the present invention differs from previously proposed fixed balloon on a guidewire systems by providing a fixed balloon on a guidewire extension wire system and kit including an extension wire and a connector assembly as well as a pair of wire cutters, or similar tool, which is used to cut-off a hub and strain-relief sleeve at the proximal end of a fixed balloon on a guidewire so that the cut end can be inserted into the connector assembly for fixing the extension wire to the fixed balloon on a guidewire.

SUMMARY OF THE INVENTION

According to the invention there is provided an extension wire for a fixed balloon on a guidewire comprising a length of extension wire and a connector assembly mounted on the distal end of the length of extension wire. The connector assembly includes a tube which is fixed to a distal end of the length of extension wire and has means within the tube for grippingly engaging an outer covering sheath of a cut proximal end of the sheath and core wire of a fixed balloon on a guidewire.

Further according to the invention there is provided a fixed balloon on a guidewire extension wire assembly kit comprising a length of extension wire and a connector assembly at the distal end of the extension wire. The connector assembly includes a tube which has a portion at one end received on and fixed to the distal end of the extension wire and which has gripping means within the tube for grippingly engaging the outer sheath of a cut proximal end of a fixed balloon on a guidewire. An alignment tool including a body and having a through-bore is adapted to receive the tube of the connector assembly at the distal end of the extension wire in one end thereof and the cut proximal end of a fixed balloon on a guidewire in the other end thereof for guiding the cut end into the tube of the connector assembly.

Also according to the present invention there is provided a method for extending an initially inserted fixed balloon on a guidewire having a strain relief sheath and a hub at the proximal end thereof. The method includes the steps of:

providing an extension wire with a connector assembly at a distal end thereof, the connector assembly including a tube fixed to the distal end of the extension wire, providing gripping means within the tube;

cutting the strain relief sheath and hub from the proximal end of an initially inserted fixed balloon on a guidewire; and inserting the cut proximal end of the fixed balloon on a guidewire including a core wire and a surrounding sheath into the tube to cause the gripping means therein to grippingly engage the sheath at the cut proximal end of the fixed balloon on a guidewire.

BRIEF DESCRIPTION OF THE DRAWINGS

FIG. 1 is a diagrammatic plan view of a patient undergoing catheterization for heart artery angioplasty and shows a fixed balloon on a guidewire inserted percutaneously into and through the femoral artery to the heart, the fixed balloon on a guidewire and an extension wire protruding proximally, and shows an extension wire;

FIG. 2 is an enlarged longitudinal sectional view of distal and proximal end portions of a fixed balloon on a guidewire with portions broken away;

FIGS. 6–10 illustrate the steps of the method of the present invention for connecting a fixed balloon on a guidewire extension wire to an inserted fixed balloon on a guidewire with:

FIG. 6 showing a medical practitioner cutting the proximal end of a fixed balloon on a guidewire to remove a strain relief sleeve and hub;

FIG. 7 showing the medical practitioner inserting the connector assembly at the distal end of the extension wire into the alignment tool;

FIG. 8 showing a cross-section of the alignment tool with the connector assembly therein;

FIG. 9 showing the medical practitioner inserting the cut proximal end of the inserted fixed balloon on a guidewire into the alignment tool; and FIG. 10 showing a longitudinal cross-section of the alignment tool with the cut proximal end of the fixed balloon on a guidewire being inserted into the connector assembly positioned within the alignment tool.

DESCRIPTION OF THE PREFERRED EMBODIMENTS

Figure 3:
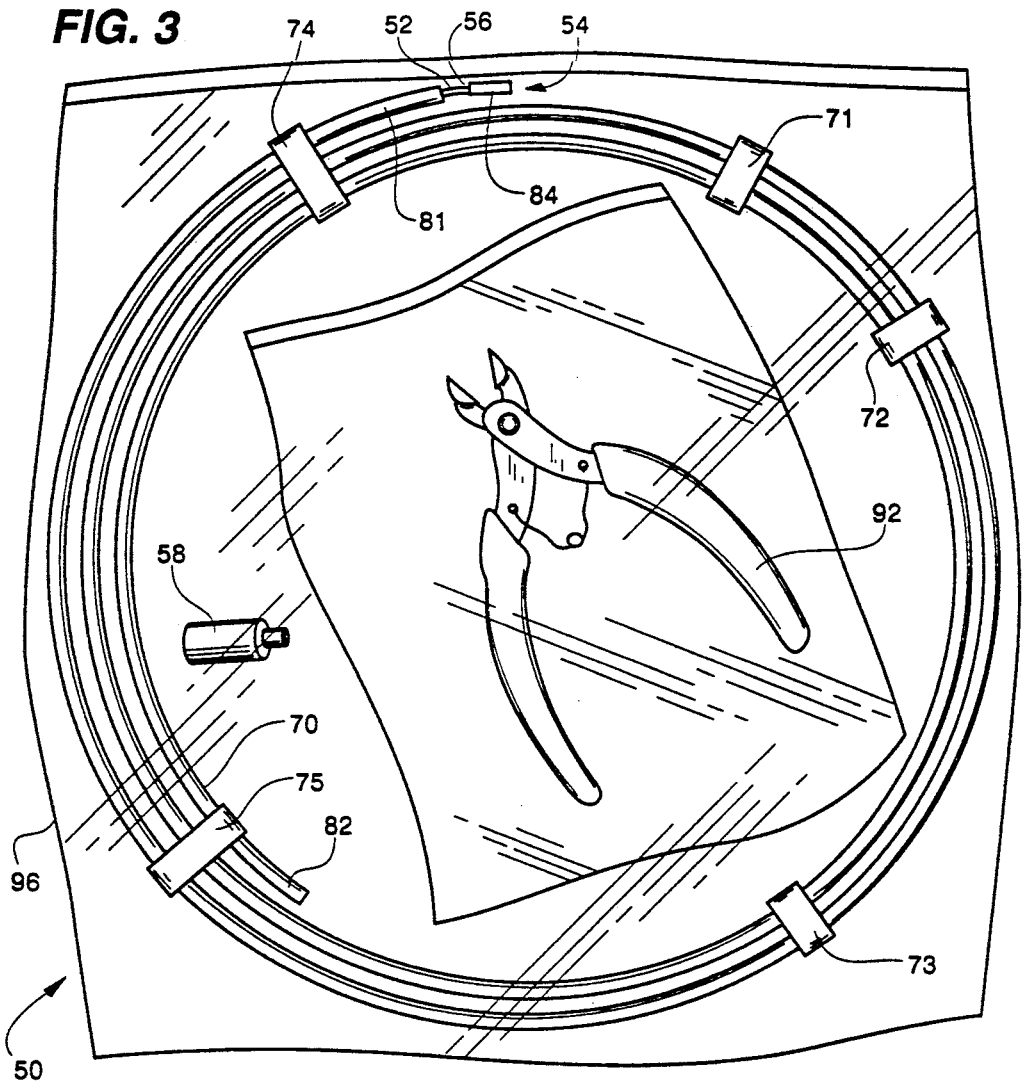
FIG. 3 is a plan view of the fixed balloon on a guidewire extension wire kit constructed in accordance with the teachings of the present invention received in a sterile pouch.

Referring now to FIG. 1 there is illustrated therein a patient 10 undergoing catheterization for heart angioplasty. For this purpose a fixed balloon on a guidewire 12 had been inserted percutaneously into and through the femoral artery 14 into the heart 16. Then a balloon 18 on the fixed balloon on a guidewire 12 situated in a heart blood vessel is placed in an area of stenosis in the heart blood vessel and dilated or expanded.

An enlarged view of a distal end portion 20 of the fixed balloon on a guidewire 12 having the balloon 18 is shown in FIG. 2. Also shown is a proximal end portion 22 of the fixed balloon a guidewire.

From FIG. 2 it will be seen that the fixed balloon on a guidewire 12 includes a central core wire 24 having mounted at the distal end 26 thereof, a thin wall flexible sleeve 28 of plastic material which has an enlarged portion 30 forming the balloon 18. A distal end portion 32 of the sleeve 28, distally of the balloon 18, is sealingly fixed to the core wire 24. Then, a slightly thicker sheath 34 of plastic material is received over and fixed to the outer surface of a proximal end portion 36 of the flexible sleeve 28 and extends axially and proximally to and through a strain relief sleeve 37 to a hub 38 at the proximal end 22 of the fixed balloon on a guidewire 12.

The outer sheath 34 of plastic material has an inner diameter larger than the outer diameter of the core wire 24 so that an annular space 42 between the core wire 24 and the outer sheath 34 of plastic material provides a passageway for supplying dilatation fluid to the balloon 18, it being understood that the proximal end portion 36 of the flexible sleeve at the distal end portion 20 of the fixed balloon on a guidewire 12 is not fixed to the core wire 24 whereby dilatation fluid can flow axially between the core wire 24 and the proximal end portion 36 of the flexible sleeve 28 into the balloon 18 for the inflation of same.

In use, the distal end portion 20 of the fixed balloon on a guidewire 12 is moved to an area of stenosis within a blood vessel. Then, a dilatation fluid is supplied through the annular space 42 between the outer sheath 34 and the core wire 24 to the balloon 18 for inflating or dilating same thereby to press the stenotic build-up outwardly against the walls of the blood vessel thereby to open the restricted passageway through the stenotic area. Once this has been achieved, the fixed balloon on a guidewire 12 is withdrawn.

Often the size of the fixed balloon on a guidewire 12 chosen is the wrong size, the balloon 18 being too small or to large. When this occurs, it is necessary to remove the fixed balloon on a guidewire 12 and replace the same with a new fixed balloon on a guidewire 12. This usually requires repeating the complete fixed balloon on a guidewire insertion procedure which is tedious, time consuming and has some risk to the patient. It would be easier if the fixed balloon on a guidewire 12 could be left in place and a guiding catheter be inserted over the initially inserted fixed balloon on a guidewire 12 followed by withdrawing the fixed balloon on a guidewire and inserting a new fixed balloon on a guidewire 12 or a dilatation catheter and guidewire. However, the presence of the hub 38 in the proximal end portion 22 of the fixed balloon on a guidewire 12 has heretofore been an obstacle to performing the procedure described above.

The fixed balloon on a guidewire extension wire system kit 50 (FIG. 3) and method of the present invention enable this desired procedure to be performed. In this respect, the fixed balloon on a guidewire extension wire kit 50 and method of the present invention provide for the cutting off the proximal end portion 22 of the fixed balloon on a guidewire having the hub 38 and any strain relief sleeve 37 from the fixed balloon on a guidewire 12. Then, a fixed balloon on a guidewire extension wire 52 having a connector assembly 54 at a distal end 56 (FIG. 4A) thereof is fixed, with the aid of an alignment tool 58 to the cut proximal end 60 (FIG. 9) of the initially inserted fixed balloon on a guidewire 12.

Then, a guiding catheter (not shown) can be inserted over the extended fixed balloon on a guidewire extension wire 52 and initially inserted fixed balloon on a guidewire 12 followed by removal of the fixed balloon on a guidewire 12 and extension wire 52 followed by insertion of a new fixed balloon on a guidewire 12 or a dilatation catheter and guidewire (not shown).

It is desirable that the connection or attachment of the connector assembly 54 at the distal end 56 of the extension wire 52 to the cut proximal end 60 of the fixed balloon on a guidewire 12 be simple while maintaining a firm attachment or connection between the extension wire 50 and the cut proximal end initially inserted fixed balloon on a guidewire 12.

The fixed balloon on a guidewire extension wire 52 and connector assembly 54 constructed according to the teachings of the present invention achieves this function, and the position of the initially inserted fixed balloon on a guidewire 12 is never lost.

As shown in FIG. 1, the fixed balloon on a guidewire extension wire 50 must have a sufficient length L, e.g. 125 cm. so that a guiding catheter of sufficient length can be inserted over the extension wire 52 and the fixed balloon on a guidewire 12 and then into the femoral artery 14 over the initially inserted fixed balloon on a guidewire 12.

Referring now to FIG. 3, there is illustrated therein the fixed balloon on a guidewire extension wire kit 50 including a coiled plastic dispensing tube 70 which is held in a coiled position by five (5) holders 71–75 each of which has at least two (2) slots (hidden from view) therethrough for receiving and holding sections of the plastic tube 70 in a coiled arrangement. Holders 74 and 75, each having three slots therein hold end portion 81 and 82 of the coiled tube 70. The distal end 56 of the extension wire 52 extends from upper outer end 81 of the coiled tube 70.

The fixed balloon on a guidewire extension wire 52 is mounted in the coiled tube 70 and a small diameter tube 84, i.e., a tube 84 having the diameter of a hypodermic needle, is mounted to the distal end 56 of the extension wire 52. The tube 84 defines and forms part of the connector assembly 54.

The kit 50 further includes the alignment tool 58 which is described in greater detail in connection with FIGS. 5 and 7-10.

Still further, the kit 50 includes a wire cutter 92 or similar tool received in a plastic bag 94 and that plastic bag 94 with the wire cutter 92 therein, the coiled tube 70 with the fixed balloon on a guidewire extension wire 52 situated therein, and the alignment tool 90 are stored in a sterile pouch 96.

Figure 4A:
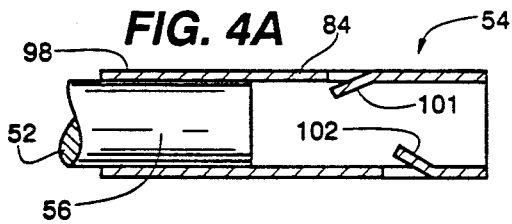
FIG. 4A is a longitudinal sectional view of a connector assembly at the distal end of the extension wire.
Figure 4B:
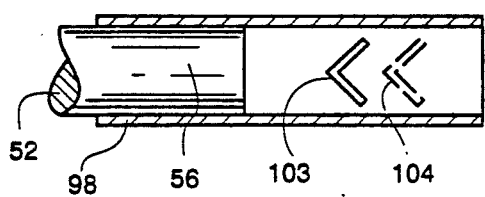
FIG. 4B is a longitudinal sectional view through the connector assembly shown in FIG. 4A rotated 90°.

As shown in FIGS. 4A and 4B, one end 98 of the tube 84 of the connector assembly 54 is fixed, such as by welding, to the distal end 56 of the fixed balloon on a guidewire extension wire 52. Also as shown, several detents 101, 102 are punched inwardly of the wall of the tube 84 to form at least two (2) teeth 103, 104 extending angularly into the tube 84 and toward the distal end 56 of the fixed balloon on a guidewire extension wire 52.

The tube 84 preferably has an inner diameter of approximately 0.0335 inch and the detents 101 and 102 extend approximately 0.045 inch into the tube 84.

Figure 5:
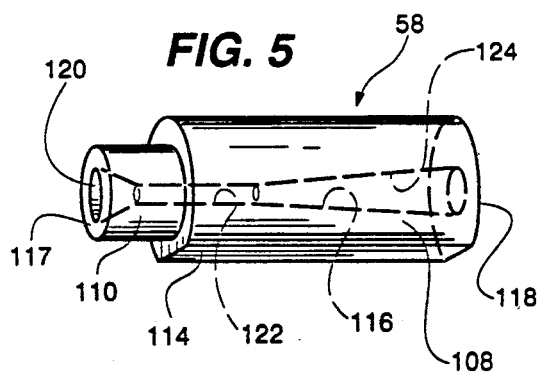
FIG. 5 is a perspective view of an alignment tool of the kit shown in FIG. 3.

Referring now to FIG. 5, there is illustrated therein the alignment tool 58 which is utilized for aligning the connector assembly 54 comprising the tube 84 with the detents 101, 102 mounted on the distal end 56 of the extension wire 52 with the cut end 60 of the fixed balloon on a guidewire 12 including the core wire 24 with the sheath 34 of plastic material thereon. As shown, the alignment tool 58 has a generally cylindrical body 108 with a reduced-in-diameter portion 110 at one end, a flat 114 on one longitudinal side thereof, and a throughbore 116 therein extending from one end surface 117 to an opposite end surface 118. The tool 58 is adapted to be gripped by the hands or placed on a flat surface and the tube 84 of the connector assembly 54 is inserted into one end 120 of the throughbore 116 which opens onto the end surface 117 of the reduced-in-diameter portion 110. As shown, the through bore 116 tapers or flares radially outwardly at the end 120 onto the end surface 117 of the reduced-in-diameter portion 110. Then the through bore 116 has a uniform diameter portion 122 extending into the body 108 of the alignment tool 58 to a tapered end portion 124 which tapers or flares radially outwardly at a smaller angle for a distance from the uniform diameter portion 122 to the opposite end surface 118 of the alignment tool 58.

The cut proximal end 60 of the initially inserted fixed balloon on a guidewire 12 is inserted into the tapered end portion 124 of the through bore 116.

Figure 6:
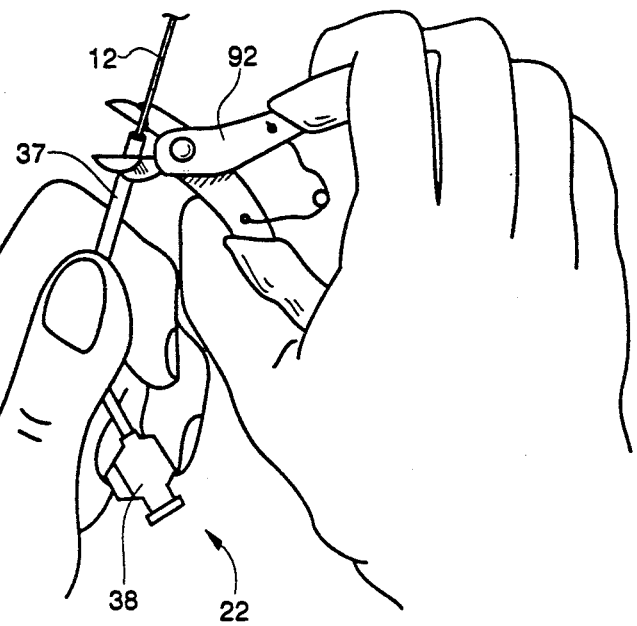

In the use of the fixed balloon on a guidewire extension wire kit 50 and in the practice of the fixed balloon on a guidewire extension wire method, a medical practitioner will first cut off the hub 38 and strain relief sleeve 37 in the proximal end portion 22 of the inserted fixed balloon on a guidewire 12 as shown in FIG. 6 using the pair of cutters 92.

Figure 7:
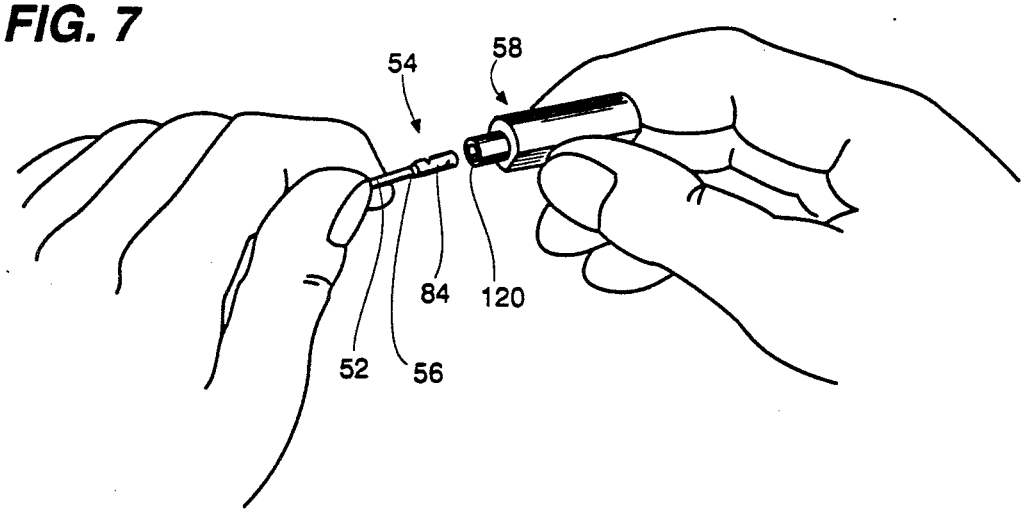

Then, gripping the alignment tool 58 as shown in FIG. 7 the medical practitioner inserts the tube 84 of the connector assembly 54 into the tapered or flared end portion 120 of the through bore 116 opening onto the axial end surface 117 of the reduce-in-diameter portion 110.

Figure 8:
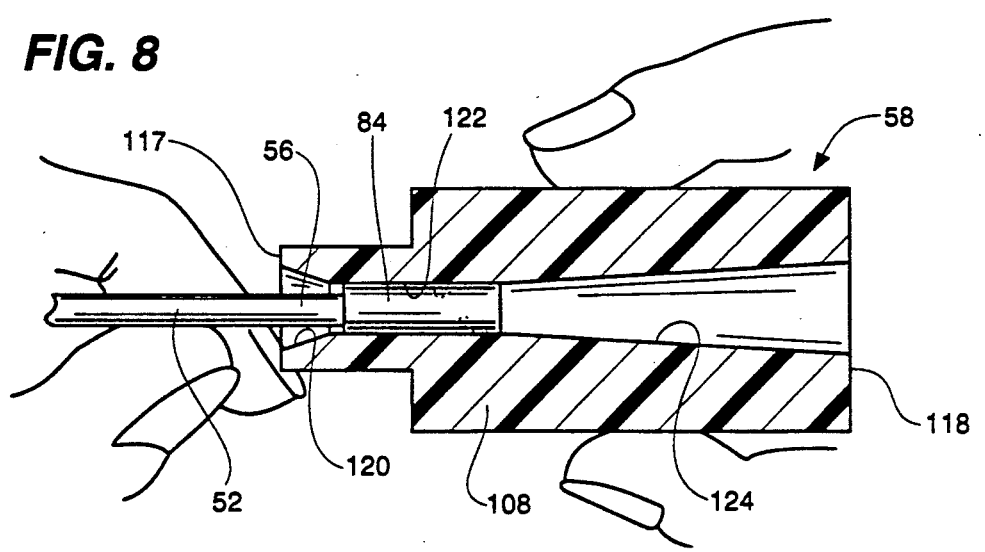

As shown in FIG. 8, the tube 84 of the connector assembly 54 is inserted into the uniform diameter portion 122 of the through bore 116.

Figure 9:
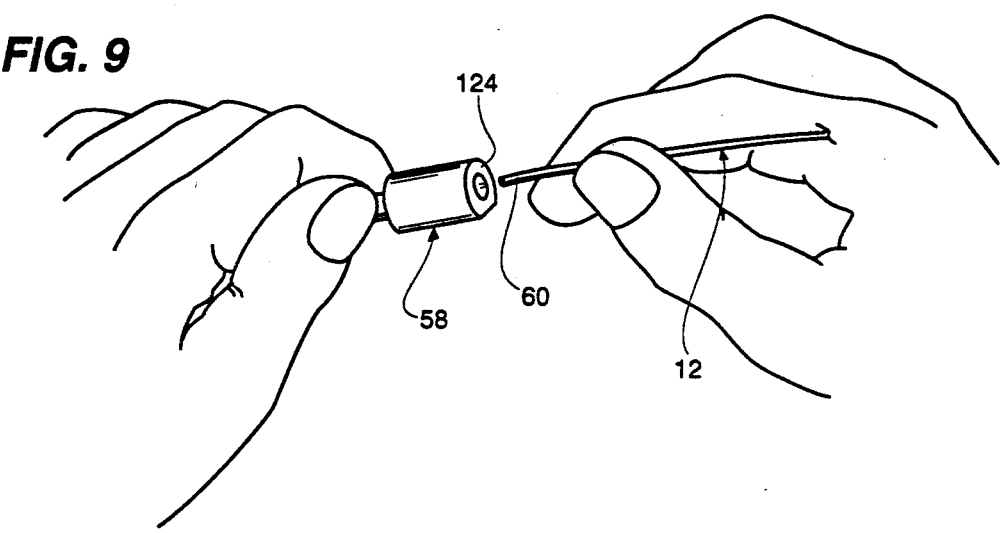
Figure 10:
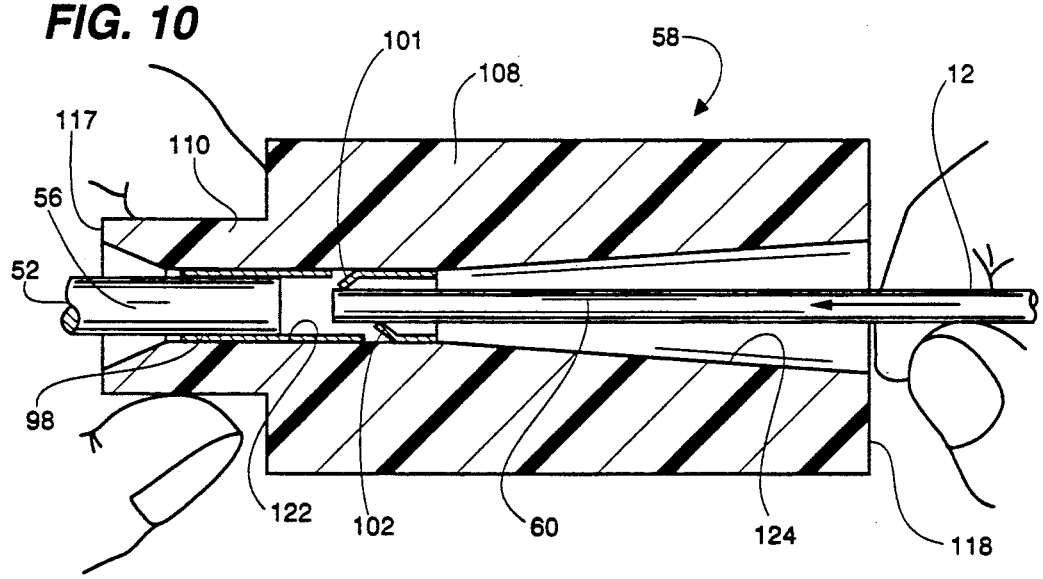

Next, the medical practitioner, grasping the reduced-in-diameter end portion 110 of the alignment tool body 108 in one hand, inserts into the longer tapered end 124 of the through bore 116, the cut proximal end 60 of the initially inserted fixed balloon on a guidewire 12 as shown in FIGS. 9 and 10.

Figure 11:
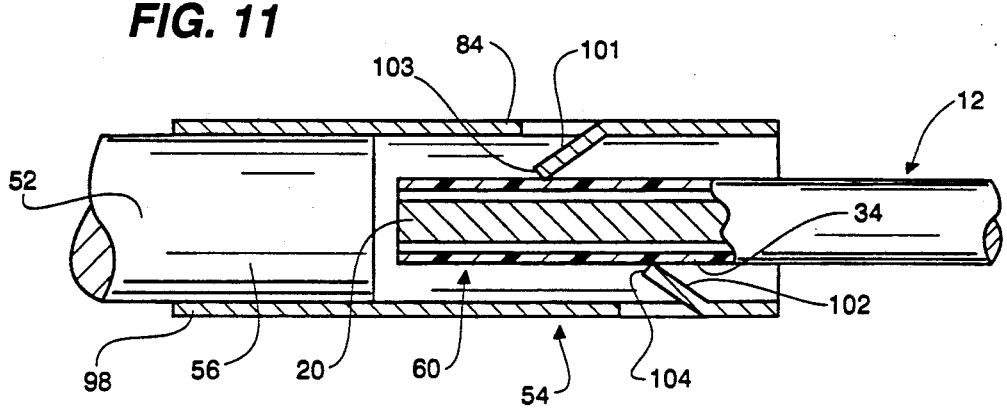
FIG. 11 is a longitudinal sectional view with portions broken away of the connector assembly with the cut proximal end of the fixed balloon on a guidewire fixed therein.

As shown in FIG. 10, the cut proximal end 60 of the fixed balloon on a guidewire 12 is inserted into the tube 84 of the connector assembly 54 and past the teeth 103, 104 until the cut proximal end 60 of the fixed balloon on a guidewire 12 bottoms against the distal end 56 of the extension wire 52 as shown in FIG. 11. In this position, as shown in FIG. 11, the teeth 103, 104 will engage, "dig into" the plastic sheath 34 around the core wire 24.

Now, the medical practitioner will pull the extension wire 52 out of the coiled tube 70 while holding the alignment tool 58 until the extension wire 52 has been completely removed from the coiled tube 70.

Then a guiding catheter can be inserted over the extension wire 52 and over the fixed balloon on a guidewire 12 and through the femoral artery 14 after which the fixed balloon on a guidewire 12 can be removed for the insertion of a different size fixed balloon on a guidewire 12 or of a dilatation balloon catheter and guidewire.

The recommended procedure for the use of the fixed balloon on a guidewire extension wire 52 and kit 50 is as follows:

1. Use the fixed balloon on a guidewire extension wire 50 only with a compatible fixed balloon on a guidewire 12.

2. Open the sterile pouch 96 slowly. To prevent damage to the connector assembly 54 and to prevent the extension wire 52 from springing onto a non-sterile field, carefully remove the extension wire 52 from the dispensing tube 70. Open the pouch 94 containing the trimming cutters 92 and remove the cutters 92.

Caution: Before use, flush all devices entering the vascular system with sterile, heparinized saline or similar isotonic solution.

3. Pull a vacuum (negative pressure) on the fixed balloon on a guidewire hub 38 to completely deflate the in vivo balloon 18.

4. Remove connectors from the fixed balloon on a guidewire hub.

5. Cut the fixed balloon on a guidewire just distal to the strain relief sleeve 37, using the trimming cutters 92. Discard the proximal catheter section with hub 38 and strain relief sleeve 37.

6. Insert the reduced-in-diameter end portion 110 of the alignment tool 58 over the connector tube 84 of the extension 52 and push until the connector tube 84 reaches the start of the long taper, i.e., about ¼ inch (FIG. 8). Insert the cut open end 60 of the fixed balloon on a guidewire 12 into the other end of the alignment tool 58. Push the extension wire 52 until the cut end 60 is fully seated in the connector tube 84 (FIG. 11). Remove the alignment tool proximally.

Note: Do not torque or manipulate the extension wire 52. The extension wire 52 does not possess the torquing characteristics of the fixed balloon on a guidewire 12. Torquing of the extension wire could result in inadvertent disengagement of the extension wire 52 from the cut end 60.

7. The fixed balloon on a guidewire 12 now can be exchanged and a new fixed balloon on a guidewire or a dilatation catheter and guidewire installed.

The fixed balloon on a guidewire extension wire 52, kit 50 and method of the present invention have a number of advantages some of which have been described above and others of which are inherent in the kit and method. Additionally, modifications can be made to the fixed balloon on a guidewire extension wire kit and method without departing from the teachings of the present invention. Accordingly, the scope of the invention is only to be limited as necessitated by the accompanying claims.

We claim:

1. An extension wire assembly for connecting to a proximal end of a fixed balloon on a guidewire which has a sheath, a core wire in the sheath and a balloon at a distal end of the sheath, said extension wire assembly comprising a length of extension wire and a connector assembly mounted on the distal end of said length of extension wire, and said connector assembly including a tube which is received on and fixed to said distal end of said length of extension wire and which has means extending inwardly within aid tube for grippingly engaging an outer covering of a cut proximal end of the sheath and core wire of the fixed balloon on a guidewire.

2. The extension wire assembly of claim 1 wherein said gripping means comprises teeth forming detents punched inwardly into the tube and having teeth points extending angularly radially inwardly and axially toward the distal end of said length of extension wire.

3. A guidewire extension wire assembly kit for connecting to a fixed balloon on a guidewire which has a sheath, a core wire in the sheath and a balloon at a distal end of the sheath, said kit comprising an extension wire assembly including a length of extension wire, a connector assembly at the distal end of said extension wire, said connector assembly including a tube, which has a portion at one end received on and fixed to the distal end of said extension wire and which has gripping means extending inwardly within said tube for grippingly engaging the outer sheath of a cut proximal end of the fixed balloon on a guidewire, and an alignment tool including a body and a throughbore adapted to receive said tube of said connector assembly at said distal end of said extension wire in one end thereof and the cut proximal end of the fixed balloon on a guidewire in the other end for guiding said cut and into said tube of said connector assembly.

4. The kit of claim 3 wherein said gripping means inside said tube comprises at least two (2) teeth forming detents which are punched in from the outer surface of said tube so as to form teeth extending radially inwardly within the tube and pointing toward said distal end of said extension wire.

5. The kit of claim 3 wherein said throughbore in said alignment tool body tappers radially outwardly at each end thereof.

6. The kit of claim 3 wherein said alignment tool body is generally cylindrical and said throughbore includes a tapered end portion which opens onto one axial end surface of said alignment tool body, (b) a uniform diameter portion and (c) a tapered portion which extends axially and radially outwardly to an opposite axial end surface of said alignment tool body.

7. The kit of claim 3 wherein said alignment tool body is generally cylindrical in shape and has an axially extending flat.

8. The kit of claim 3 further including a cutting tool.

9. The kit of claim 8 wherein said cutting tool is a pair of pliers which is received in a plastic bag.

10. The kit of claim 3 including a coiled tube and said extension wire is mounted in said coiled tube.

11. The kit of claim 3 including a sterile pouch and wherein the components of said kit are received in said sterile pouch.

12. A method for extending an initially inserted fixed balloon on a guidewire including a sheath, a core wire in the sheath, and a balloon at the distal end of the sheath and having a strain relief sleeve and a hub at the proximal end of the sheath, said method including the steps of:

providing a connector assembly including a tube having gripping means extending inwardly within said tube;

cutting the strain relief sleeve and hub from the proximal end of the initially inserted fixed balloon on a guidewire; and inserting the cut proximal end of the fixed balloon on a guidewire including the core wire and surrounding sheath into the tube of the connector assembly to cause the gripping means therein to grippingly engage the sheath at the cut proximal end of the fixed balloon on a guidewire.

13. The method of claim 12 including the step of providing an alignment tool having a through bore and wherein said step of inserting said cut proximal end of the initially inserted fixed balloon on a guidewire is accomplished by first inserting the tube of the connector assembly at the distal end of the extension wire into one end of the throughbore followed by inserting the cut proximal of the initially inserted fixed balloon on a guidewire into the other end of the throughbore of the alignment tool and then into the tube at the distal end of the extension wire.

14. The method of claim 13 including the step of providing the throughbore in the alignment tool with axially and radially outwardly extending tapered or flared end portions.

* * * * *

UNITED STATES PATENT AND TRADEMARK OFFICE
CERTIFICATE OF CORRECTION

PATENT NO. : 5,139,032

DATED : August 18, 1992

INVENTOR(S) : Scott L. Jahrmarkt, Fernando M. Viera, William Box

It is certified that error appears in the above-identified patent and that said Letters Patent is hereby corrected as shown below:

Column 4, line 56 "cm." should be --cm.,--

Column 8, line 7 "a" should be --(a) a--.

Signed and Sealed this

Twenty-fifth Day of January, 1994

*Attest:*

BRUCE LEHMAN

*Attesting Officer*     *Commissioner of Patents and Trademarks*